United States Patent [19]
Salt

[11] 3,957,450
[45] May 18, 1976

[54] ARTICLE OF MANUFACTURE WITH PRE-DETERMINED FATIGUE LIFE

[75] Inventor: Trevor L. Salt, Beverly, Mass.

[73] Assignee: General Electric Company, Lynn, Mass.

[22] Filed: July 29, 1974

[21] Appl. No.: 492,859

Related U.S. Application Data

[62] Division of Ser. No. 323,348, Jan. 15, 1973, Pat. No. 3,908,447.

[52] U.S. Cl. .............................. 29/180 R; 416/219 A
[51] Int. Cl.² ............................................ B21K 3/04
[58] Field of Search ............... 416/219, 241, 244; 73/91; 29/407, 180

[56] References Cited
UNITED STATES PATENTS

| | | | |
|---|---|---|---|
| 3,045,968 | 7/1962 | Willis | 416/219 X |
| 3,576,681 | 4/1971 | Barker et al. | 416/241 X |
| 3,744,300 | 7/1973 | Fleury | 73/91 X |

*Primary Examiner*—Everette A. Powell, Jr.
*Attorney, Agent, or Firm*—James W. Johnson, Jr.; Derek P. Lawrence

[57] ABSTRACT

Fatigue failure of an engineering article is primarily influenced by a natural inherent defect in the material from which the article is made. By an ability established to allocate a quantitative measure to such defect as a new material property influenced only by environment and material manufacturing procedures as are other basic properties, and using known methods for determining critical stress areas, a wide range of fatigue design data can be generated from a few basic measurements. Thus, from the deduction of a characteristic material defect length, there can be determined both a material's basic fatigue properties and the fatigue capability of the article for which the material is used.

4 Claims, 10 Drawing Figures

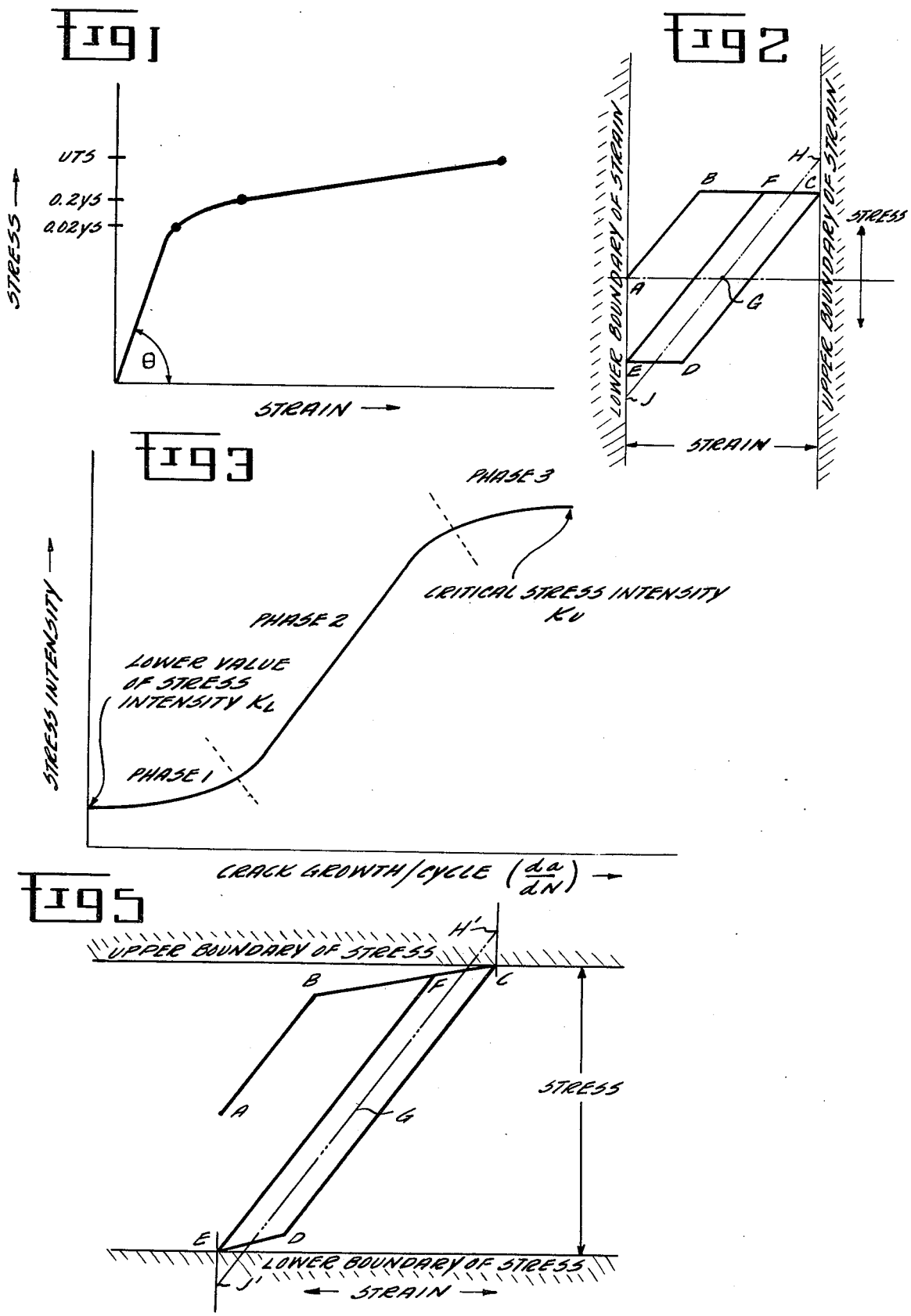

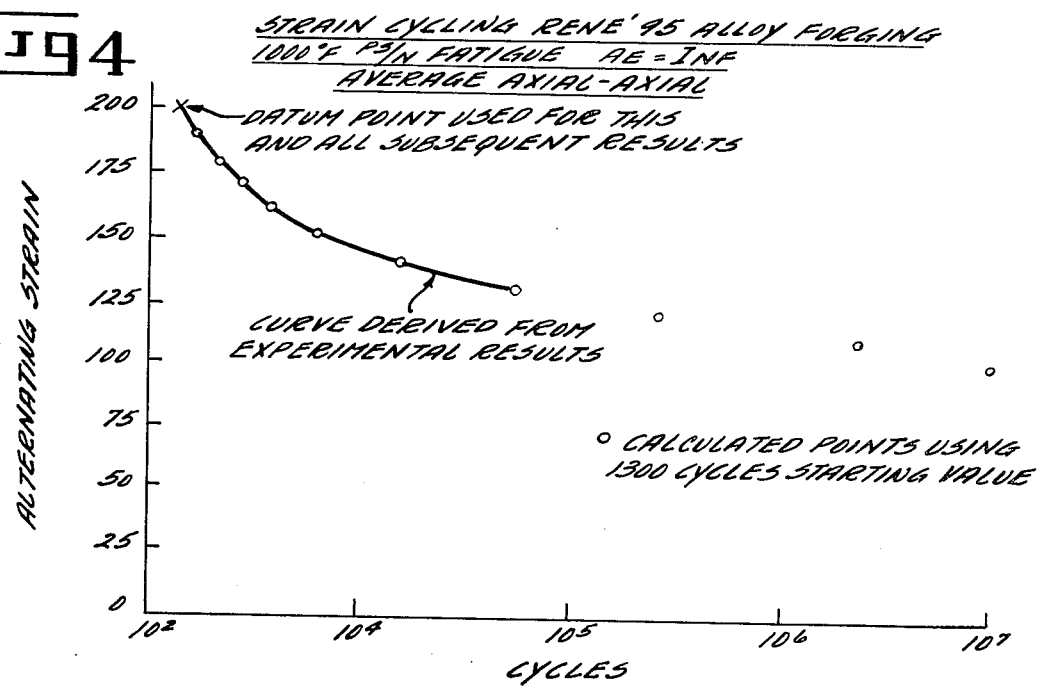
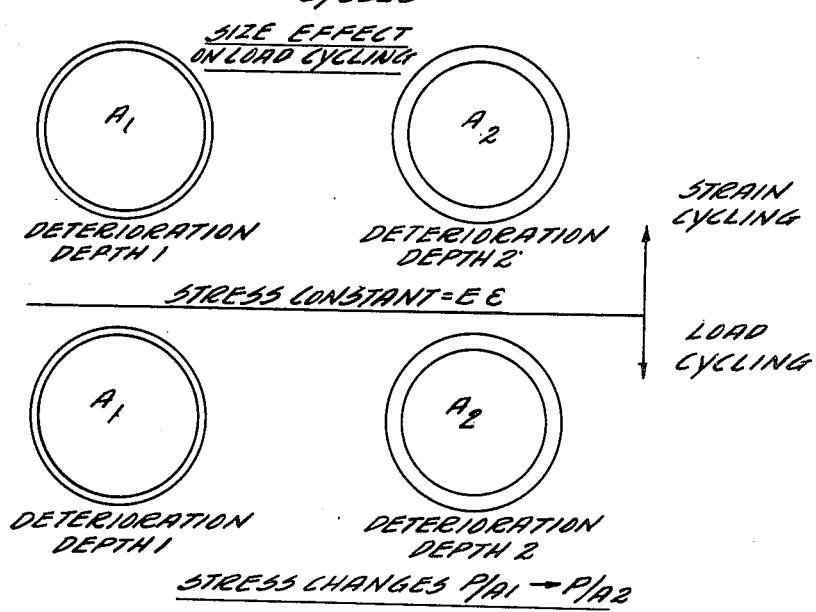

DISC RIM POST
DOVETAIL SLOT

ARTICLE OF MANUFACTURE WITH PRE-DETERMINED FATIGUE LIFE

This is a divisional application of application Ser. No. 323,348 filed Jan. 15, 1973, now Pat. No. 3,908,447, and assigned to the assignee of the present invention.

BACKGROUND OF THE INVENTION

This invention relates to an article of manufacture and methods for making the article and for determining the useful life of an article. More particularly, it relates to a determination of an article's fatigue capability.

A serious problem faced by the designer of an article is the selection of a configuration sufficient for the material of construction of the article to prevent fatigue failure under the article's intended operating conditions for a desirable period of time. Because fatigue of materials is extremely complex and fatigue failures common, it is the subject of extensive investigation at considerable expense. Yet is is commonly accepted that there is still no completely acceptable design prediction technique.

Basic material properties, such as yield strength, ultimate tensile strength, reduction in area and Young's modulus, as well as a variety of interrelationships between properties, such as that relating stress intensity to crack growth rate under selected conditions, are data generally determined during the development of the material itself. However, it has been advisable for many critical articles to determine the fatigue characteristics of a designed article by testing the article itself prior to its introduction into actual service and, in certain difficult applications, by observing the performance of the article during actual operation. This, of course, is a very time-consuming and costly method for determining the fatigue characteristics of the article.

SUMMARY OF THE INVENTION

It is a principal object of the present invention to provide a method for exploring the fatigue characteristics of a material, and an improved life prediction method for an article designed to use such material, utilizing only basic material data from which the theoretical stress/strain relationship can be determined, known methods for determining critical stress areas, and the mechanism for the initiation and progression of a material's defect which ultimately, under fluctuating stresses, can lead to fatigue fracture.

A more specific object is to provide such a method, generating data more accurate than that attained by other methods, and which can be used to determine the design allowable limits of combinations of mean stress and alternating stress.

Still another object is to provide a method for making an article having at least a minimum selected useful fatigue life under selected operating conditions without actually operating the article under such conditions.

A further object is to provide an article of manufacture designed to withstand a selected number of operating cycles.

These and other objects and advantages will be more clearly understood from the following detailed description, the examples and the drawing, all of which are intended to be representative of, rather than in any way limiting on, the scope of the present invention. It will be recognized that the present invention can be applied with articles made of any material.

Briefly, the present invention, in one form, provides a method for determining the period of use of an article under selected environmental conditions and under determined design stresses before such article, made of a known material, should be replaced. An important aspect of this method is the determination of the article's characteristic material defect length ($\lambda$). This is done by utilizing basic material data and a single observed failure data point for any selected fatigue property which is desired to be explored.

The method of the present invention can be used to determine the useful life of an article and can be used in the manufacture of an article designed to withstand a selected number of operating cycles. The article of the present invention thus is configured to develop in a maximum design stress portion, a stress related to the characteristic material defect length according to a relationship including a parameter also characteristic of the matter and structure making up such article.

The method in one more specific form involves determining, by at least one of a variety of known and widely used and reported experimental or analytical stress analysis techniques, the critical area or areas of peak stresses in an article which is to be used under selected environmental and operating conditions. Examples of such experimental stress analysis include photoelastic techniques; examples of analytical methods include the finite element stress analysis technique. Also determined is the characteristic material defect length of the material from which the peak stress area of the article is made. Then, knowing these two, the useful life of the article is forecast by applying the characteristic material defect length in the peak stress area and, using known fracture mechanics techniques with variations in stress related to crack length, measuring the cycles to which the article can be subjected before failure occurs from the peak stress area.

Determination of the characteristic material defect length involves first obtaining observed stress/strain data from which the material's stress/strain diagram can be constructed. From this, a theoretical stress/strain relationship is constructed between selected design limits of stress or strain. This factors in defect characteristics of the material, and using actual data, represents the theoretical relationship because the presence of inherent material defects coupled with basic material data normalizes or removes the influence of such defects. Then an equivalent linear relationship representing such theoretical stress/strain relationship is selected. Also obtained with preliminary data is the observed relationship between stress intensity and crack growth rate so that a typical diagram relating stress intensity (SI) to crack growth rate per cycle ($da/dN$) can be constructed. The last item of observed or actual data required for determination of the characteristic material defect length is an actual observed failure data point for any selected fatigue property under a selected stress condition.

From these data, the effective length ($\lambda$) of a characteristic material defect is determined by selecting at random a first material defect length and then using known fracture mechanics techniques to determine if the length fits the single observed failure data point for the selected fatigue property. If it does not fit, then a series of substitute lengths are selected in turn, in an iterative process, until the calculated results coincide, to the degree desired, with the actual failure data point. With the characteristic material defect length thus established, other fatigue properties can be calculated under different selected stresses to generate a complete life curve without additional physical testing.

BRIEF DESCRIPTION OF THE DRAWING

FIG. 1 is a graphical presentation of one form of a relationship between stress and strain;

FIG. 2 is a simplified theoretical, schematic presentation of a hysteresis loop generated by cycling between strain limits;

FIG. 3 is a graphical presentation of the relationship between stress intensity and crack growth rate;

FIG. 4 is a graphical presentation of an example of the comparison between actual smooth specimen fatigue values and values obtained according to the present invention under strain cycling conditions;

FIG. 5 is a simplified, theoretical schematic presentation of a hysteresis loop generated by cycling between stress limits;

FIG. 6 is a diagrammatic comparison of article size effect on load cycling;

DESCRIPTION OF THE PREFERRED EMBODIMENTS

Figure 7:
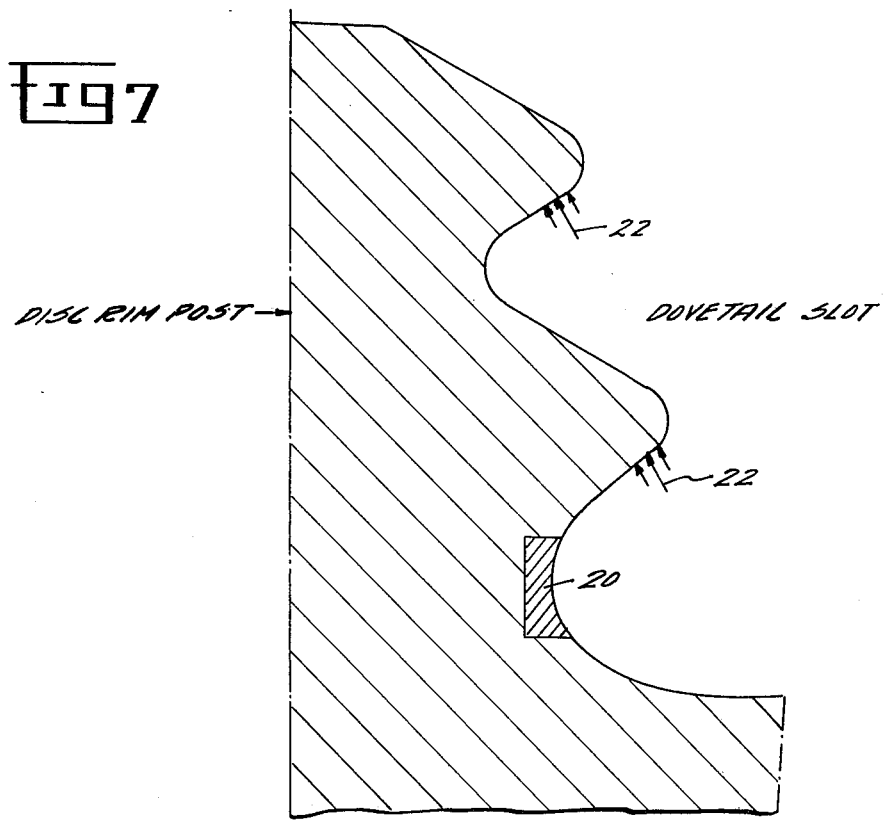
FIG. 7 is an enlarged, fragmentary sectional view of one half of an article of manufacture, specifically a turbine disc dovetail slot and disc rim post, showing an area of peak stress.

The fatigue of materials and their fracture is believed to be principally a function of their local weaknesses and imperfections. In metals and alloys, these may be associated with grain boundaries and grain size or internal metallurgical precipitates. In any event, it is well known that the theoretical strength of a material, which may be several times that attainable in its use in an article, may be demonstrated with whiskers of extreme purety. It is hypothesized that the slope of the stress/-strain curve at the origin represents an indication of this theoretical strength which decays to the commonly observed stress/strain behavior by the presence of natural defects.

Thus in reality, there is never a truly linear relationship between stress and strain for common materials although a concept of elasticity is often a reasonable assumption, within certain limits, for design purposes. Furthermore, it is believed that there is no endurance limit for any common materials; it is just that some materials deviate less from the theoretical stress/strain line at low stresses by nature of their less significant defect characteristics.

In accordance with the present invention, it is important to assess the influence of the defect characteristic of an article's material relative to the material's basic theoretical strength in obtaining solutions for failure under many varying conditions. This assessment may be achieved using principles of fracture mechanics and stress analysis with the assumption that each material has a characteristic material defect and that this defect can be utilized in the same manner as the crack propagation of fracture mechanics. Such defect will be purely a material property and as such will vary only with environment and material manufacturing procedures as do other common material properties.

The size of the material characteristic defect, as a mean value, may be expressed as a depth from the surface of the material and in many cases in respect to metals will bear a qualitative relationship to grain size. For example, in high strength steels it will be only a few thousandths of an inch.

The application of the characteristic material defect length, which can be called ($\lambda$), recognizes stages of damage in a material. In introducing fracture mechanics theory, the principal phases of damage are identified by the commonly derived plot of crack growth per cycle with stress intensity at the crack tip, the stress intensity being a function of the stress at the crack tip and the length of the crack. According to one aspect of the method of the present invention, the characteristic material defect, which is a linear dimension of something which behaves like a crack but otherwise is not normally identifiable nor measurable directly as such by micrographic techniques, is an essential element of such an analysis. Such characteristic material defect can be considered to be an inherent crack even though it may be of the nature of a grain boundary or metallurgical precipitate which would not normally be categorized as a crack by the usual defect inspection.

The present invention will be more clearly understood from the following detailed examples which represent its application to metal alloys. However, as has been stated before, the present invention is generally applicable in the exploration of fatigue properties of an article of any material including but not limiting to metals, their alloys or composites, non-metallic composites, or their combinations.

One alloy with which the method of the present invention was used is a high temperature nickel base superalloy described in U.S. Pat. No. 3,576,681 - Barker et al, issued Apr. 27, 1971, and sometimes referred to as Rene' 95 alloy. It was decided to determine the effective length ($\lambda$) of the characteristic Rene' 95 material defect at 1000°F. The average basic material data at that temperature in air, determined by oridinary and well-known metallurgical techniques, is a 0.02% yield strength of 139 ksi, a 0.2% yield strength of 159 ksi, an ultimate strength of 201 ksi, a reduction of area of 10% and Young's modulus of $26.5 \times 10^6$ psi. As used herein, "ksi" means thousands of pounds per square inch and "psi" means pounds per square inch. From these basic material data, the stress/strain relationship of the type shown in FIG. 1 was constructed from observed discrete points.

Since such a stress/strain diagram is in this form because of its particular defect characteristics, it is fist necessary to obtain the equivalent theoretical stress/-strain relationship when considering cycling between fixed design limits, for example, strain limits. In this example, the lower and upper boundaries of strain were selected to be $+200,000/28.6 \times 10^6$ and $-200,000/28.6 \times 10^6$ in/in, respectively. Utilizing the basic material data used to generate a stress/strain relationship as is shown in FIG. 1, and cycling in sequence between the lower and upper boundaries of strain, the hysteresis loop, EFCD in the theoretical schematic view of FIG. 2 was established by passing through points A, B, C, D, E, F and back to C. According to one feature of the method of the present invention, the equivalent theoretical stress/strain relationship for cycling between the two selected limits of strain, in this example, is the linear relationship represented by line JH in FIG. 2.

Because of the frequent complex stages of elasticity in materials, the establishment of an equivalent theoretical stress/strain relationship may require several cycles. In practice, it is generally established by no more than about 10 such cycles to provide a relationship of sufficient accuracy. As was mentioned, the establishment of the basic observed stress/strain diagram for use in this procedure for any given material may be obtained from the basic material properties of yield strength, ultimate strength, reduction of area and Young's modulus. This factors in the defect characteristics of the material. Thus, using actual data, the equivalent stress/strain relationship represented by line JH in FIG. 2 is the theoretical stress/strain relationship because the presence of inherent material defects coupled with basic material data removes the influence of such defects.

With the removal of the influence of inherent defects, it is now possible to apply them to the theoretical stress/strain linear relationship by the known principles of fracture mechanics in obtaining the deterioration in fatigue and fracture. However, additional data must be obtained in order to define the relationship between stress intensity and crack growth rate. Obtainable by widely used and well-known testing techniques are the upper value of limiting critical stress intensity $K_{t'}$ and the lower value of stress intensity $K_L$, as well as the points intermediate those extremes, to define an observed relationship between stress intensity (SI) and crack growth rate ($da/dN$) as shown in FIG. 3. For the Rene' 95 alloy in this example, at 1000°F, the parameters of $K_{t'}$ and $K_L$ were found to be 75 ksi $\sqrt{in.}$ and 11.5 ksi $\sqrt{in.}$, respectively, the dimension ksi being associated with stress and the dimension " $\sqrt{in.}$" being associated with crack length in the relationship $K = C\sigma \sqrt{a}$. In addition, as an observed data point for cycles to failure, it was found that ± 200,000 psi (strain × Young's modulus) gave 1300 cycles to failure.

Having obtained these basic data all by known testing techniques on the material itself, in this case a smooth bar, the effective length ($\lambda$) of the characteristic material defect can be determined. In this example, a first characteristic defect length of 0.010 inch was selected at random. As is well known in the fracture mechanics art, the general relationship for the stress intensity factor K recognizes that such factor is a function of stress at the tip of the crack and the square root of its length. This relationship can generally be expressed as $K = C\sigma \sqrt{a}$ in which K is the stress intensity factor, C is a constant related to article geometry, sigma ($\sigma$) is the stress and $a$ is the crack length. Using the equivalent linear relationship represented by line JH in FIG. 2, sigma values are those of the maximum and minimum stresses. The term $a$ is the randomly selected first characteristic material defect length. The term C is determined by exact stress analysis for the article shape. Therefore, the curve of the shape of FIG. 3 can be traversed by incrementally increasing the crack length $a$, for example, as by 1% steps, to determine the quantity $dN$ in the crack growth per cycle portion of the diagram of FIG. 3. This is the number of cycles consumed going through that incremental length increase chosen. As the length increases, new stress intensity values will be determined. This procedure is repeated for a series of increasing crack lengths $a$ until the value for critical stress intensity $K_{t'}$ is reached. The sum of all of the cycles is the calculated number of cycles to failure based on the randomly selected first characteristic material defect length. If the total number of cycles does not coincide with the single failure data point, for example 1300 cycles for Rene' 95 alloy at 1000°F, then the randomly selected value for the characteristic defect length is incorrect. If the number of cycles is too few, then the selection for the length of the characteristic defect is too long and, therefore, a shorter length must be selected for the next step in the iteration. Similarly, if the number of cycles to failure is too many, then the randomly selected length for the characteristic defect is too short and the next selected length in the iteration must be longer. When the number of cycles obtained approaches the actual number of cycles in the observed failure data point, to the degree selected for accuracy, then the characteristic defect length ($\lambda$) for the material under the selected environmental conditions has been obtained according to one feature of the method of the present invention. In the example for Rene' 95 alloy at 1000°F, the characteristic material defect length was found to be 0.003 inch.

It will be appreciated by those familiar with the art, that after obtaining the basic material data, generating the stress/strain and stress intensity vs. crack growth rate relationships, and obtaining a physically observed failure data point for a selected fatigue property, all by known testing techniques widely used in the art, the balance of the method of determining the characteristic material defect length is most conveniently conducted by a computer programmed to operate in a digital manner.

In a preferred method of determining the characteristic material defect length, the diagram of FIG. 3 can be constructed more simply from the data for the lower value of stress intensity $K_L$ and for the critical stress intensity $K_{t'}$ as two important points. Further, it may be shown that on a log log basis, each phase may be assumed to be linear. In addition, it is an experimentally observed fact that many cyclic crack growth rate curves, particularly for metallic materials, on a log log basis show fourth power relationship from about $10^{-6} < da/dN < 10^{-2}$ inches per cycle. Therefore, phase 2 may be given a constant slope relating to the common fourth power observation of crack propagation for many diverse matrials. Thus, it is assumed that phase 1 represents microscopic damage, phase 2 macroscopic damage and phase 3 gross damage.

Having obtained the effective length of the characteristic material defect, it can be used along with the parameters for critical stress intensity $K_{t'}$ and the lower value of stress intensity $K_L$ to obtain total strain cycling information using the relationship $K = C\sigma \sqrt{a}$, varying $\sigma$ to determine the number of cycles to failure. For example, at a stress ratio, A, of infinity in which a pseudo stress of ±200 ksi was alternated about a mean of 0, the points circled in FIG. 4 were calculated. It is readily seen that there is an extremely close correlation between these calculated data points and the continuous line in FIG. 4 which was generated by mechanical testing.

Although this example has been directed to obtaining strain cycling information, it should be understood that load cycling information can be obtained in a similar manner by generating an equivalent linear relationship such as line JH in FIG. 2 but by cycling between limits of stress rather than limits of strain. Such an equivalent theoretical stress/strain relationship is shown in FIG. 5 in which line J'H' represents the equivalent linear relationship. Thus, in the determination of load cycling characteristics, the value for J'H' determined between boundaries of stress is substituted for that determined between boundaries of strain in solving the stress intensity value as previously described.

In respect to application of the characteristic material defect length ($\lambda$), according to the present invention, in load cycling data determinations, there should be introduced a specimen or article size consideration. This is necessary because the average stress on the cross section in load cycling increases as the outer material becomes cracked and therefore is destroyed, but remains constant under strain cycling. Therefore, the size adjustment described in FIG. 6 should be introduced for load cycling and explains why strain cycling and load cycling results are not equal even at high numbers of cycles.

In considering more complex geometries of actual engineering articles intended to serve in a selected environment and in cyclic operation, for example dynamic energy conversion apparatus one type of which would include turbomachinery articles, rather than simplified laboratory test specimens, the characteristic material defect length is utilized in coordination with the particular stress fields existing in the article. More particularly, it is utilized, according to one form of the present invention, where the stresses are influenced by engineering notches which may be characterized in turbomachinery as bolt holes, fillets, dovetails and the like. The total stress fields required may be derived, as was mentioned before, from the observations of photoelastic testing or by application of modern techniques of finite element stress analysis.

One turbomachinery article with which the method of the present invention has been used is a turbine disc dovetail slot and a disc rim post which cooperate to restrain a turbine blade. An enlarged, fragmentary, sectional view of one such article is shown in FIG. 7. An area in the disc rim post identified as an engineering notch is shown at 20. Such area is subject to peak stresses as a result of the application of force, represented by arrows 22, to the disc rim post.

Figure 8:
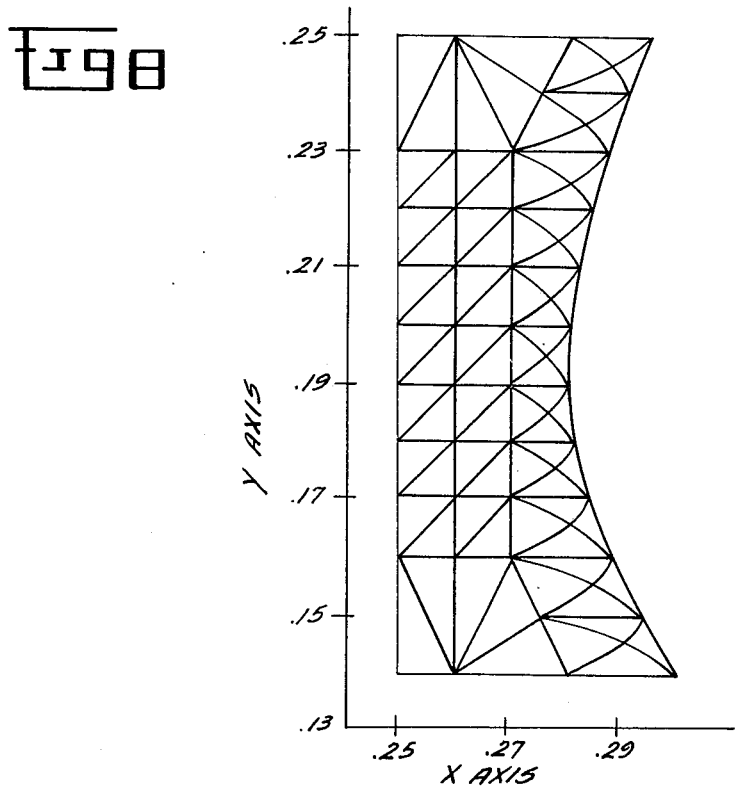
FIG. 8 is a graphical presentation of an analytical model of the area of peak stress of FIG. 7 in the form required for finite element stress analysis.
Figure 9:
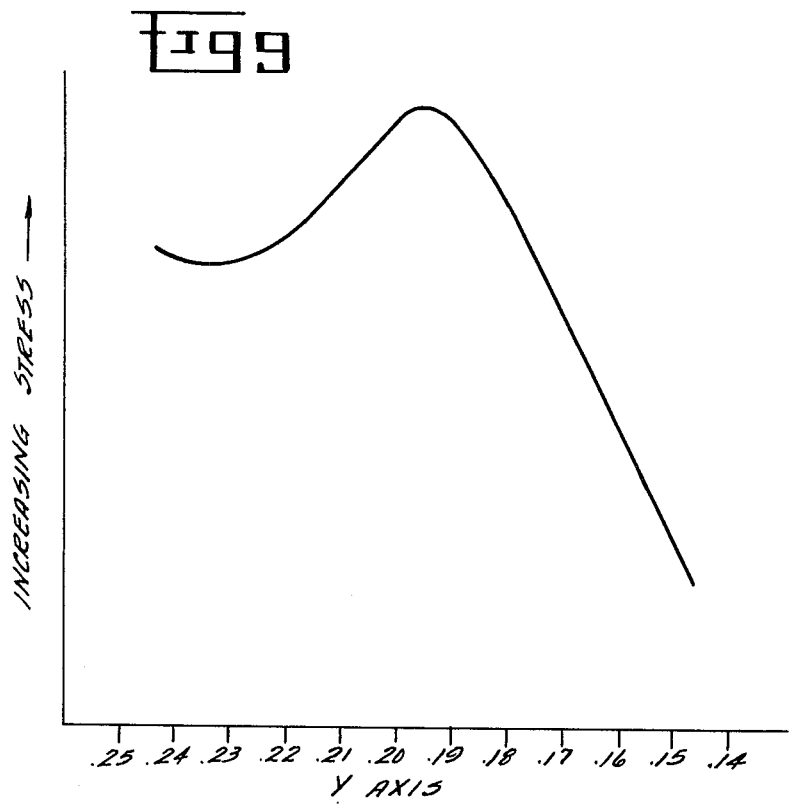
FIG. 9 is a graphical presentation of a typical variation of stress level in the area of peak stress of FIG. 7 using the model of FIG. 8 to locate the peak surface stress.

Derivation of the maximum stresses in an area such as 20 in FIG. 7 can be accomplished through the well-known finite element stress analysis technique. This technique utilizes a peak stress area analytical model of the type shown in FIG. 8. It is initially of interest to know the point at which the maximum stress would occur along the surface of peak stress area 20. Therefore, the geometric figures, in this case triangles, into which the particular model of FIG. 8 is divided, all are made essentially the same size along the surface and generally smaller than those beneath the surface. In this manner, stresses that are all at the same distance inward from the surface are being compared. A typical variation of stress at the centroid in all of the model's triangular elements adjacent the surface is shown in FIG. 9. In this particular example, the peak surface stress is shown to occur along the Y axis at 0.195 on the model. As will be appreciated by those skilled in the art of fracture mechanics and stress analysis, other models or combinations of models can be used to identify such peak stress point.

Figure 10:
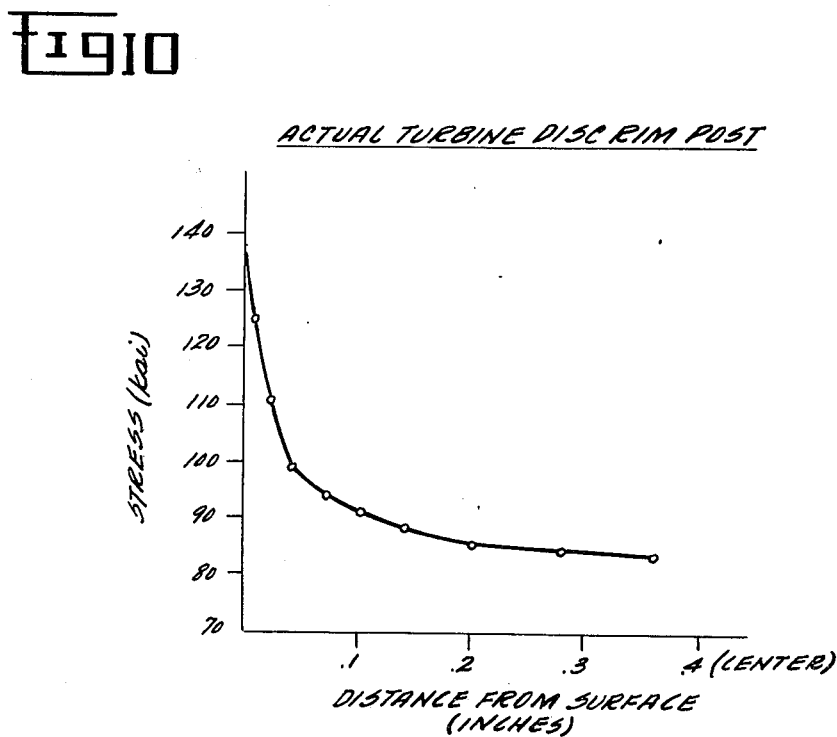
FIG. 10 is a graphical presentation of the variation of the peak stress with increasing distance from the surface.

Similarly, there can be determined the variation of stress, at that peak stress location on the article, with increasing distance from the surface. As an example of such a determination, an actual gas turbine engine turbine disc rim post was evaluated for operation at 1000°F. The material of the article was a nickel base superalloy, sometimes identified as IN718, and having a nominal composition, by weight, of 0.05%C, 19%Cr, 18.5%Fe, 3%Mo, 5%Cb/Ta, 1%Ti, 0.5%Al, with the balance essentially Ni and incidental impurities. Data from a finite element stress analysis technique used in this example is summarized in FIG. 10 comparing stress with distance from the surface of area 20 in FIG. 7 at the peak stress point.

With this information concerning a critical stress area in the article, it was then necessary for practice of the method of the present invention to determine the length ($\lambda$) of the characteristic material defect for IN718 alloy at 1000°F in the manner described in detail in this description. Basic material data, determined by usual mechanical testing techniques included a 0.02% yield strength of 128.6 ksi, a reduction of area of 4% and Young's modulus of 26.3 × 10$^6$. The value for upper limiting critical stress intensity $K_U$ was 100 ksi $\sqrt{in}$ and for the lower stress intensity $K_L$ was 12 ksi $\sqrt{in}$. The observed failure data point was 2000 cycles low cycle fatigue at ±175 ksi. From such basic material data, the characteristic material defect length ($\lambda$) for this particular material at 1000°F was found to be 0.0092 inch.

With this knowledge of the stress analysis of the article and the characteristic defect length of the material of the article, the method of the present invention of forecasting the useful life of the article without further testing can be practiced using ordinary and well-known fracture mechanics techniques using the above-described relationship $K = C \sigma \sqrt{a}$. This is initiated by recognizing that crack initiation will start in the peak stress location at a distance beneath the surface equal to the characteristic material defect length ($\lambda$). From the data summarized in FIG. 10, the initial stress field at that point beneath the surface can be determined. The method of the present invention of determining the expected useful life of an article under the selected operating conditions proceeds by measuring the number of cycles to failure utilizing initially the stress data represented by FIG. 10. When the product of stress times the square root of crack length exceeds the upper value of limiting critical stress intensity $K_U$, failure occurs. Also, the number of cycles to any selected crack length depth, for example 0.015 inch deep crack, can be determined in this manner.

As an example of the close correlation between the method of the present invention and actual observed data, the IN718 alloy disc in a slot configuration of the type shown in FIG. 7 was run at 975°F and under a radial load of 40 ksi. Actual cracks were observed after 15,500 cycles. The method of the present invention forecast cracks of 0.015 inch length to exist under those conditions at an average of 12,100 cycles and failure was predicted for an average of 21,300 cycles.

Engineering articles of manufacture, one example of which is turbomachinery components discussed above, generally are designed to have at least a selected useful fatigue life during operation. If, through practice of one aspect of the method of the present invention in the manufacture of the article, its fatigue life is determined to be less than he minimum selected for that article, the design can be changed, thus reshaping the article, to reduce the stress in a critical area in order to increase life. This can be done in a variety of ways, for example, by changing the contour of a fillet or by reshaping or eliminating cavities or holes until the reduced stresses provide at least the desired useful life. Thus the article of manufacture according to the present invention is designed to with stand in a particular environment an approximate number (N) operational cycles prior to failure. It is configured to develop in a maximum design stress portion a stress which is related to the characteristic material defect length ($\lambda$). Also, the number of cycles to failure is a function not only of such length ($\lambda$), which includes parameters of material of construction, but also of the configuration or structure of such article. This relationship can be expressed as $N \approx E(\lambda P)$, where $P$ is a parameter also characteristic of the matter and structure making up such article.

Although the present invention has been described in connection with specific examples, articles and metallic materials, those skilled in the arts to which the invention relates will recognize the complexity of the subject matter and, hence, the breadth to which the invention can be applied. For example, the invention can be applied with any material and with any article configuration, the stresses in which are capable of anaylsis. In addition, it recognizes that such stresses can be analyzed in a wide variety of ways. It is intended to cover in the appended claims the variations of which the method of the present invention is capable in the process of designing and manufacturing an article for practical use.

What is claimed is:

1. An article of manufacture intended to serve in an environment in which it is required to have a minimum useful fatigue life in a maximum stress portion wherein the article is manufactured by the process of:
   selecting a material for construction of the article;
   obtaining stress/strain data for the selected material;
   obtaining stress intensity crack growth data for the selected material;
   obtaining experimentally a characteristic material defect length ($\lambda$) for the selected material by:
   a. obtaining at least one measured fatigue characteristic for the selected material;
   b. selecting at random a first characteristic material defect length ($\lambda$) for the selected material; and then
   c. applying $\lambda$ to the stress/strain data and the stress intensity crack growth data to obtain fatigue characteristics and then
   d. comparing the measured fatigue characteristics with the fatigue characteristics obtained by applying $\lambda$ to the stress/strain and stress intensity crack growth data, and modifying the selected value for $\lambda$ until these fatigue characteristics match;
   making an initial design for the article;
   applying $\lambda$ to the stress/strain data and the stress intensity crack growth data to determine the useful fatigue life of the article in the maximum stress portion of the initial design; and
   making the article to the design if the useful fatigue life is at least said minimum or reshaping the design of the maximum stress portion until the minimum useful fatigue life is attained and then making the article to the reshaped design.

2. The article of claim 1 in which the determination of the characteristic material defect length ($\lambda$) comprises the steps of:
   obtaining for the selected material a stress/strain relationship from observed discrete points;
   constructing from known material test data the equivalent theoretical stress/strain relationship for cycling between two limits of items selected from the group of items consisting of stress and strain, the relationship having an equivalent linear relationship;
   obtaining for the selected material an observed relationship between stress intensity (SI) and crack growtn per cycle ($da/dN$);
   obtaining as the fatigue characteristic an observed failure data point for the selected material at a first selected stress; and then
   determining the effective length ($\lambda$) of the characteristic material defect by:
   a. selecting at random a first characteristic defect length;
   b. using the equivalent linear relationship for the theoretical stress/strain relationship and the observed relationship between SI and $da/dN$ to determine if the first selected defect length fits the data for the observed failure data point for the selected fatigue property; and
   c. repeating the determination if no fit occurs by selecting substitute defect lengths until a desired fit occurs with the observed failure data point.

3. The method of claim 2 in which the material is tested to obtain data for yield strength, ultimate strength, reduction in area and Young's modulus to obtain the stress/strain relationship.

4. The method of claim 2 in which the relationship between SI and $da/dN$ is constructed;
   using a lower value of stress intensity ($K_L$) as an initial point;
   using an upper value of limiting critical stress intensity ($K_{t'}$) as a final point, and then
   constructing the relationship as a series of three connected substantially straight lines, the first of which starts at $K_L$, the last of which terminates at $K_{t'}$ and the intermediate of which has a constant slope relating to a common fourth power observation of crack propagation.

* * * * *